United States Patent [19]

Rittersdorf et al.

[11] Patent Number: 5,215,924
[45] Date of Patent: Jun. 1, 1993

[54] METHOD FOR THE DETERMINATION OF AN ION WITH INCREASED SENSITIVITY, USE OF SUBSTANCES WHICH ARE SUITABLE FOR THIS AND A CORRESPONDING AGENT

[75] Inventors: Walter Rittersdorf; Werner Guethlein; Detlef Thym, all of Mannheim; Peter Vogel, Hemsbach, all of Fed. Rep. of Germany

[73] Assignee: Boehringer Mannheim GmbH, Mannheim, Fed. Rep. of Germany

[21] Appl. No.: 698,465

[22] Filed: May 10, 1991

[30] Foreign Application Priority Data

May 15, 1990 [DE] Fed. Rep. of Germany ....... 4015592

[51] Int. Cl.$^5$ ..................... G01N 33/50; G01N 33/20; G01N 21/00; A61K 3/16
[52] U.S. Cl. ........................................ 436/68; 436/74; 436/164; 514/608; 514/614; 514/639; 514/731; 514/732; 564/250; 564/251; 568/716; 568/719
[58] Field of Search ............................ 436/68, 74, 164; 514/609, 614, 639, 731, 732; 564/250, 251; 568/716, 719

[56] References Cited

U.S. PATENT DOCUMENTS 3,800,051 3/1974 Barnhart et al. .................... 424/246
4,990,633 2/1991 Negele et al. ...................... 549/551

FOREIGN PATENT DOCUMENTS 0343441 11/1989 European Pat. Off. .

OTHER PUBLICATIONS

G. Brown, et al., Chem. Abst. 87: 193625k, 1977.
P. Juvvik, et al., Chem. Abst. 79: 15265b, 1973.
Brown, G., et al. Eur. J. Med. Chem.-Chim. Therap. 12:361–363 (1977).
Juvvik, e al. J. Chrom. 84:414–416 (1973).

*Primary Examiner*—John W. Rollins
*Attorney, Agent, or Firm*—Felfe & Lynch

[57] ABSTRACT

The invention relates to a method for determining an ion in an aqueous sample. The method involves contacting the sample with a water immiscible material including an ionophore, a pH indicator and a compound which stabilizes sensitivity of the assay. The ion reacts with the ionophore in the water immiscible material, releasing a proton which reacts with the pH indicator generating a color change which is representative of the ion to be measured. The stabilizing compound stabilizes this change. Also described are compositions including the three recited elements, and various new compounds useful as the stabilizer.

7 Claims, 2 Drawing Sheets

METHOD FOR THE DETERMINATION OF AN ION WITH INCREASED SENSITIVITY, USE OF SUBSTANCES WHICH ARE SUITABLE FOR THIS AND A CORRESPONDING AGENT

Figure 1:
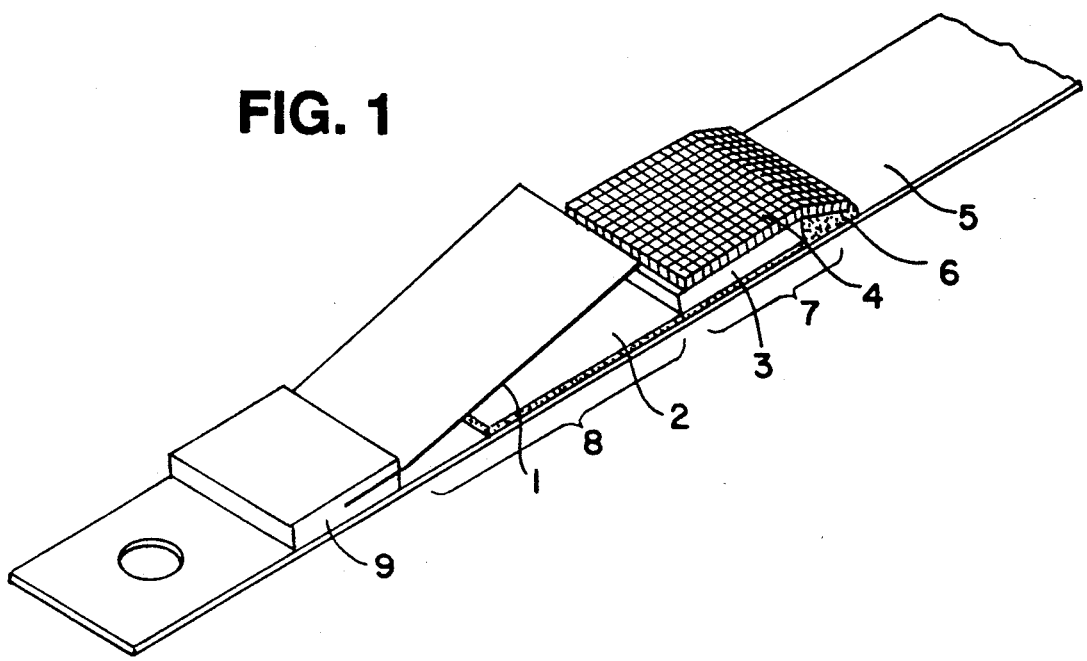
FIG. 1 shows a test strip useful for the method according to the invention.

The invention concerns a method for the determination of an ion in an aqueous liquid, in particular a body fluid such as blood, plasma, serum or urine, in which the ion passes into a phase which is immiscible with the aqueous liquid and as a result a pH indicator which is present there undergoes a colour change which is used for the determination of the ion. In addition, the invention concerns the use of substances which lead to an increase in the measurement sensitivity of such a method. The invention also concerns an agent for the determination of an ion in an aqueous liquid which contains an ionophore and a pH indicator in a medium which is immiscible with water.

A multitude of methods are known for the determination of ions in solutions, in particular alkaline and alkaline-earth ions. Flame photometry, atomic absorption spectrometry and recently also ion-selective electrodes have gained most importance in this connection. All these methods require a considerable degree of instrumentation. For this reason one has tried to look for alternatives which enable the user to determine the ions with methods which are more simple to handle. Such methods are of interest for the rapid determination of sodium ions in sea water desalination, for the rapid determination of calcium ions in water softening etc. Methods which can be carried out rapidly and are simple to handle are particularly important in the determination of sodium and potassium ions in body fluids such as blood, plasma, serum or urine in the laboratory diagnosis and emergency diagnosis of diseases of the cardiovascular system, muscle diseases, kidney diseases or states of shock of various causes etc. Lithium determinations are for example necessary in the monitoring of antidepressant therapies.

A multitude of methods which are based on liquid-liquid extraction of coloured anions are known for the simple determination of cations, such as alkaline ions, which are particularly important for the aforementioned diagnostic problems. In these methods an anionic dye is added to an aqueous solution of the cation and subsequently it is extracted by shaking with a solvent which contains an ionophore and is immiscible with water. The ionophore, which is a complexing agent for alkaline ions, pulls the ion together with a proportional amount of dye into the liquid phase which is immiscible with water. After removing the aqueous phase (with the excess dye), the organic phase is then analysed photometrically.

Although this method is widely used in wet chemistry it is of little use for the so-called dry chemistry. This term is understood to include test carriers, also named rapid diagnostics, in which all of the reagents which are required for the test reaction are present in a dry state in or on one or several carrier matrices such as absorptive materials or materials which are capable of swelling. For the quantitative determination of a substance, a liquid sample is applied to the test carrier and there it is brought into contact with the reagents which are necessary for the test reaction. A measurable signal is formed as a measure for the substance to be determined. If the signal consists of a formation of colour or change in colour, this can be evaluated visually or photometrically, preferably by reflectance photometry.

The simplicity of the test carrier principle contrasts with the difficulty of having to add a dye to the sample for the determination of an ion and then to have to remove its surplus. It is therefore not surprising that such a method as disclosed in EP-A-0 041 175 has not become of importance for a dry test.

Methods of determining cations which are based on the principle of a so-called "heterogeneous pH reaction" as presented below are more suitable for test carriers.

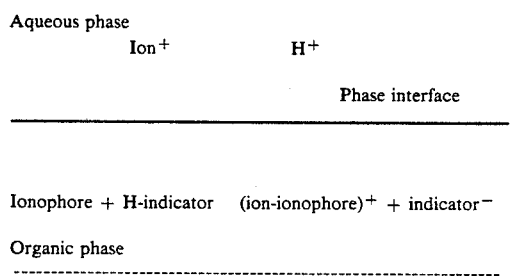

In this case a two-phase system with an aqueous and an organic phase is present. A specific ionophore for the cation to be detected and a pH indicator are dissolved in the organic phase. Both chemical species can also be present as a chromoionophore, i.e. combined via a chemical bond to form a single molecule. The ion to be detected is taken up by the ionophore at the interface of the two phases, transported into the organic phase and then is present there as an ion-ionophore complex. In order to counterbalance the charge this causes the pH indicator, which is also present in the organic phase, to release a proton which is transferred into the aqueous phase. In this way an amount of coloured indicator anion is formed which is proportional to the concentration of the ion to be detected which was originally present in the aqueous phase.

This principle was first mentioned for liquid-liquid extractions in E. S. Hyman, Biophysical Society Abstracts, 1971, 72a where valinomycin is used as the ionophore and tetrabromophenolphthalein ethyl ester as the pH indicator.

Descriptions with chromoionophores may be found for example in K. Ueno and M. Takagi, Studies in Physical and Theoretical Chemistry 27, 279–293 (1982 as well as in H. Nakamura et al., Bunseki Kagaku 31, E 131–E 134 (1982).

In the said publications the liquid-liquid extraction is used as the analysis procedure. Embodiments of rapid diagnostics for ions which are based on this principle have been described several times. They differ mainly only in the way they are carried out i.e. how the organic phase is realized in a form which is useful for rapid diagnostics. In general, in all these applications the organic phase consists of relatively non-volatile, organic liquids and/or hydrophobic polymers which are immiscible with water. If both are present as a solid solution then one also refers to them as plasticized plastics.

An embodiment is described in EP-A-0 125 555 in which the organic phase is present as a plasticized, non-polar, non-porous plastic film in which the ionophore and indicator are dissolved. In EP-A-0 175 990 hydrophilic, preferably water-soluble particles of appropriate organic polymers are embedded in an organic phase of hydrophobic, film-forming, water-insoluble polymer. A form of application is described in EP-A-0 125 554 in which the organic hydrophobic phase is in the form of small droplets which is embedded in a hydrophilic matrix. EP-A-0 153 641 describes a porous carrier matrix which is impregnated with an organic hydrophobic phase containing chromophore and ionophore. Paper is described as the preferred carrier matrix. In EP-A-0 141 647 the organic phase is described as pigmented plasticized plastic whereby chromoionophores are also used here.

The said state of the art give no indication of a solution to a general problem which can occur when evaluating ion tests which are based on the principle of the heterogeneous pH reaction. The problem is that the range of highest sensitivity of measurement not always corresponds to the clinically relevant concentration range. This is for example documented by the following: the normal range of potassium in human plasma is between 3.5 and 5.5 mmol/l. Values which are above or below the normal values have to be determined exactly. As a consequence the range of highest accuracy of the measurement procedure must cover this concentration range in order to achieve optimal analytical results. In the case of ion determinations according to the principle of the heterogeneous pH reaction this means that the colour change of the pH indicator should yield a change in signal which can be measured as well as possible in the concentration range of the ion which has to be determined. In the case of reflectance measurements this means that the change in reflectance has to be as large as possible in the concentration range of interest of the ion to be determined. This is, however, not always the case.

It should in fact be possible to shift the range for the colour change of a pH indicator and thus the range of the highest accuracy of measurement in determinations of ions according to the principle of the heterogeneous pH reaction by adding an acid to the organic phase. One could envisage the following mechanism for this: if an ion is pulled into the organic phase by the ionophore then it should only depend on the acid strength and the concentration of the acid which is present there and of the indicator where the necessary proton is cleaved off in order to maintain the balance of charge in the aqueous phase. If it is cleaved off from the acid then no colour change takes place. If in contrast it is cleaved off from the pH indicator then this causes a colour change. An acid which is more acidic than the indicator should therefore first consume ion equivalents so that the indicator causes a change in colour only at a higher concentration range of the ion.

However experiments with conventional lipophilic strong acids such as halogen-carboxylic acids, halogen- and nitrobenzolcarboxylic acids, phosphoric acid diesters and similar acids have proven that in practice these acids have almost no effect on ion determinations according to the principle of the heterogeneous pH reaction i.e. they have hardly any effect on the range of highest sensitivity.

The object of the present invention is therefore to provide substances which can be used to match the range of highest sensitivity of the heterogeneous pH reaction method to the concentration range of the ion which is to be investigated.

The invention provides a method for the determination of an ion in an aqueous liquid in which the ion passes into a phase which is immiscible with the aqueous liquid and as a result a pH indicator which is present there undergoes a colour change which can be used for the determination of an ion and which is characterized in that in order to increase the sensitivity of the measurement a substance from the group of compounds having the general formula I

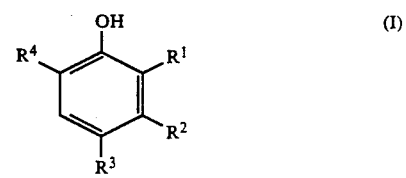

in which
one of the residues $R^1$ to $R^4$ is a residue from the group of alkyl residues, alkoxy residues and aralkyl residues and
the other residues are the same or different and each denotes a nitro group, halogen, a cyano group, an alkylsulfonyl group or an alkyl group substituted with halogen,
having the general formula II

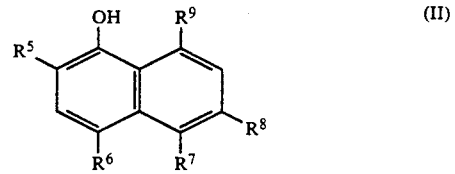

in which
one of the residues $R^5$ to $R^9$ is a residue from the group of alkyl residues, alkoxy residues and aralkyl residues and
the other residues are the same or different and each denotes a nitro group, halogen, a cyano group, an alkylsulfonyl group or an alkyl group substituted with halogen or if $R^5$ and $R^6$ represent nitro groups, $R^8$ and $R^9$ can also denote hydrogen and
having the general formula III

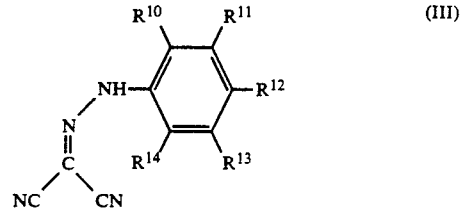

in which $R^{10}$, $R^{11}$, $R^{12}$, $R^{13}$, $R^{14}$ are the same or different and each denotes hydrogen, a nitro group, halogen, a cyano group, an alkylsulfonyl group or an alkyl group substituted with halogen, is used in the phase which is immiscible with the aqueous liquid.

A further subject matter of the invention is the use of a substance from the group of compounds having the general formula I

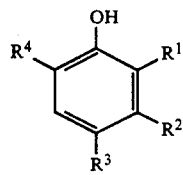

in which
one of the residues $R^1$ to $R^4$ is a residue from the group of alkyl residues, alkoxy residues and aralkyl residues and
the other residues are the same or different and each denotes a nitro group, halogen, a cyano group, an alkylsulfonyl group or an alkyl group substituted with halogen,
having the general formula II

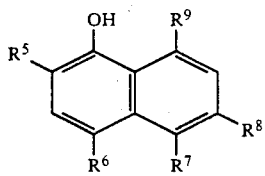

in which
one of the residues $R^5$ to $R^9$ is a residue from the group of alkyl residues, alkoxy residues and aralkyl residues and
the other residues are the same or different and each denotes a nitro group, halogen, a cyano group, an alkylsulfonyl group or an alkyl group substituted with halogen or if $R^5$ and $R^6$ represent nitro groups, $R^8$ and $R^9$ can also denote hydrogen and
having the general formula III

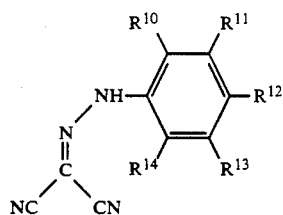

in which $R^{10}$, $R^{11}$, $R^{12}$, $R^{13}$, $R^{14}$ are the same or different and each denotes hydrogen, a nitro group, halogen, a cyano group an alkylsulfonyl group or an alkyl group substituted with halogen, in order to increase the measurement sensitivity of methods for the determination of ions.

In addition the invention provides an agent for the determination of an ion in an aqueous liquid containing an ionophore and a pH indicator in a medium which is immiscible with water which is characterized in that it contains a substance from the group of compounds having the general formula I in order to increase the measurement sensitivity

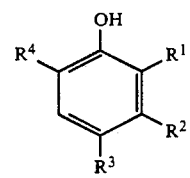

in which
one of the residues $R^1$ to $R^4$ is a residue from the group of alkyl residues, alkoxy residues and aralkyl residues and
the other residues are the same or different and each denotes a nitro group, halogen, a cyano group, an alkylsulfonyl group or an alkyl group substituted with halogen,
having the general formula II

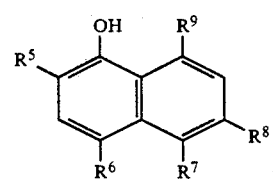

in which
one of the residues $R^5$ to $R^9$ is a residue from the group of alkyl residues, alkoxy residues and aralkyl residues and
the other residues are the same or different and each denotes a nitro group, halogen, a cyano group, an alkylsulfonyl group or an alkyl group substituted with halogen or if $R^5$ and $R^6$ denote nitro groups, $R^8$ and $R^9$ can also denote hydrogen and
having the general formula III

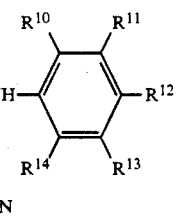

in which $R^{10}$, $R^{11}$, $R^{12}$, $R^{13}$, $R^{14}$ are the same or different and each denotes hydrogen, a nitro group, halogen, a cyano group, an alkylsulfonyl group or an alkyl group substituted with halogen.

In addition a subject matter of the invention is the use of a substance from the group of compounds having the general formula I

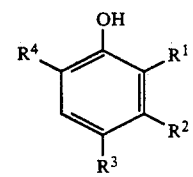

in which
one of the residues $R^1$ to $R^4$ is a residue from the group of alkyl residues, alkoxy residues and aralkyl residues and the other residues are the same or different and each denotes a nitro group, halogen, a cyano group, an alkylsulfonyl group or an alkyl group substituted with halogen, having the general formula II $$\text{(II)}$$

[Structure II: naphthalene with OH and $R^5$ on one ring, $R^6$, $R^7$, $R^8$, $R^9$ on the rings]

in which
one of the residues $R^5$ to $R^9$ is a residue from the group of alkyl residues, alkoxy residues and aralkyl residues and
the other residues are the same or different and each denotes a nitro group, halogen, a cyano group, an alkylsulfonyl group or an alkyl group substituted with halogen or if $R^5$ and $R^6$ represent nitro groups, $R^8$ and $R^9$ can also denote hydrogen and
having the general formula III $$\text{(III)}$$

[Structure III: phenyl ring with $R^{10}$, $R^{11}$, $R^{12}$, $R^{13}$, $R^{14}$ substituents, NH-N=C(CN)(CN) group]

in which $R^{10}$, $R^{11}$, $R^{12}$, $R^{13}$, $R^{14}$ are the same or different and each denotes hydrogen, a nitro group, halogen, a cyano group, an alkylsulfonyl group or an alkyl group substituted with halogen, in order to produce an agent for the determination of an ion.

The invention also provides a compound having the general formula I'

$$\text{(I')}$$

[Structure I': phenyl ring with OH, $R^{1'}$, $R^{2'}$, $R^{3'}$, $R^{4'}$ substituents]

in which
$R^{2'}$ represents an alkyl or alkoxy residue and
$R^{1'}$, $R^{3'}$ and $R^{4'}$ are the same or different and each denotes a nitro group, halogen, a cyano group, an alkylsulfonyl group or an alkyl group substituted with halogen.

The invention also provides a compound having the general formula II $$\text{(II)}$$

[Structure II: naphthalene with OH, $R^5$, $R^6$, $R^7$, $R^8$, $R^9$]

in which
$R^7$ is an alkyl, alkoxy or aralkyl residue, in particular an alkoxy residue and
the other residues are the same or different and each denotes a nitro group, halogen, a cyano group, an alkylsulfonyl group or an alkyl group substituted with halogen or if $R^5$ and $R^6$ represent nitro groups, $R^8$ and $R^9$ can also denote hydrogen.

Finally the invention provides a compound from the group of substances
[(2,3,5,6-tetrafluorophenyl)-hydrazono]propanedinitrile,
[(2-trifluoromethyl-4-nitrophenyl)-hydrazono]-propanedinitrile,
[(2-methanesulfonyl-4-nitrophenyl)-hydrazono]-propanedinitrile,
[(2,4-dinitro-6-cyanophenyl)-hydrazono]propanedinitrile
and [(3,5-di-(trifluoromethyl}phenyl)-hydrazono]-propanedinitrile.

It was surprisingly found that acids exist which, in methods for the determination of ions on the basis of the principle of the heterogeneous pH reaction, act in such a way that they can be used in the phase which is immiscible with the aqueous liquid in order to increase the sensitivity of the measurement. These are phenols and naphthols with residues which attract electrons and which carry an alkyl residue, an alkoxy residue or an aralkyl residue in order to increase the lipophilicity. In addition phenylhydrazone derivatives of mesoxalic acid-dinitrile whose phenyl residue carries electron-attracting substituents can also be used.

Compounds having the general formula I, the general formula II and the general formula III with the meaning as stated above have proven to be successful. An alkyl residue as such or which is present in an alkoxy residue in the definition of the residues $R^1$ to $R^4$ or $R^5$ to $R^9$ is understood as an alkyl residue with 1 to 30 carbon atoms. However, residues are preferred with 5 to 30, preferably 10 to 20 carbon atoms. Particularly preferred are those with 15 to 18 carbon atoms. The alkyl groups in alkyl residues as such or in alkoxy residues can be straight-chained or branched, saturated or unsaturated.

An alkyl group within the meaning of an aralkyl residue, an alkylsulfonyl group or an alkyl group substituted with halogen in the definition of the residues $R^1$ to $R^4$, $R^5$ to $R^9$ or $R^{10}$ to $R^{14}$ contains 1 to 4 carbon atoms. The methyl group is particularly preferred.

Halogen within the meaning of the residues $R^1$ to $R^{14}$ denotes fluorine, chlorine, bromine or iodine. Fluorine, chlorine and bromine are particularly preferred. Within the meaning of an alkyl group substituted with halogen in the definition of the residues $R^1$ to $R^{14}$, the trifluoromethyl group is very especially preferred.

In the definition of the residues $R^1$ to $R^9$, the aromatic residue in an aralkyl residue contains 6 to 10 carbon atoms. It is preferably hydrocarbon. The phenyl residue is very especially preferred. The aromatic moiety of an aralkyl residue is advantageously substituted by one or several electron-attracting residues such as nitro, halogen or cyano residues. A very especially preferred aralkyl residue is a benzyl residue which carries one or several electron-attracting residues. The aralkyl residue can also carry a hydroxy group apart from electron-attracting residues. Very especially preferred is namely a benzyl residue with one or several electron-attracting residues and a hydroxy group.

Preferred compounds having the general formula I are those in which $R^2$ denotes an alkyl, alkoxy or aralkyl residue and $R^1$, $R^3$ and $R^4$ are the same or different and each denotes a nitro group, halogen, cyano group, an alkylsulfonyl group or an alkyl group substituted with halogen. Those of these compounds which carry the same or different residues from the group comprising nitro residue, halogen and alkylsulfonyl group as the residues $R^1$, $R^3$ and $R^4$ are particularly suitable according to the invention.

Examples of compounds having the general formula I which are outstandingly effective are for example 3-pentadecyl-2,4,6-trinitrophenol or hexachlorophene (bis-(2-hydroxy-3,5,6-trichlorophenyl)-methane).

Preferred compounds having the general formula II are those in which $R^7$ denotes an alkyl, alkoxy or aralkyl residue, in particular an alkoxy residue and $R^5$, $R^6$, $R^8$ and $R^9$ are the same or different and each denotes a nitro group, halogen, a cyano group, an alkylsulfonyl group or an alkyl group substituted with halogen. Those compounds which carry the same or different groups from the group consisting of nitro group, halogen and alkylsulfonyl group as the residues $R^5$, $R^6$, $R^8$ and $R^9$ are particularly suitable according to the invention. Of the preferred compounds mentioned below having the general formula II, those are particularly preferred in which $R^6$ is a nitro group.

An example of a compound having the general formula II which can be used excellently according to the present invention is 2,4,6,8-tetranitro-5-octadecyloxy-1-naphthol.

Examples of compounds having the general formula III which can be used excellently according to the present invention are those in which at least two of the residues $R^{10}$ to $R^{14}$ are not hydrogen.

Compounds having the general formula I, II and III are very suitable for matching the range of greatest sensitivity of the method to the range of ion concentration in methods for the determination of an ion in aqueous liquids, in particular body fluids such as blood, plasma, serum or urine, which are based on the principle of the "heterogeneous pH reaction" as described supra. The compounds are only poorly soluble in aqueous solutions but have good solubility in organic solvents. In this respect they can be dissolved in the organic phase and can be used there for the intended purpose. It has turned out that in the presence of the acids according to the present invention, the ion concentration can be determined much more exactly via the colour change of a pH indicator than without acid.

In this sense the combination of an acid according to the present invention with a pH indicator having the general formula IV has proven to be particularly preferable

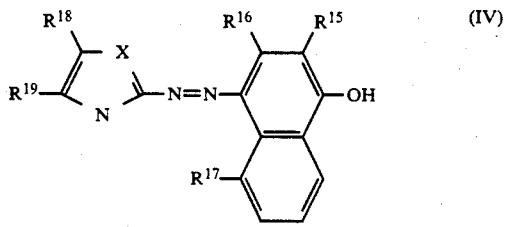

(IV)

in which $R^{15}$, $R^{16}$, $R^{17}$ are the same or different and each represents hydrogen, an alkyl or alkoxy group in which at least one of the residues is a $(C_8-C_{30})$-alkyl or alkoxy residue $R^{18}$ is hydrogen or an alkyl group $R^{19}$ is a nitro group, an alkyl group substituted by halogen, a cyano group, a sulfonamide group or an alkylsulfonyl group X is nitrogen or the residue $CR^{20}$ and Y is sulphur or the residue $CR^{21}=CR^{22}$ in which $R^{20}$, $R^{21}$, $R^{22}$ are the same or different and each denotes hydrogen, halogen, a nitro group, a cyano group, an alkyl group or an alkyl group substituted by halogen or an alkylsulfonyl group. Such pH indicators are described in DE-A-4015591.9.

An alkyl group in the definition of the residues $R^{15}$, $R^{16}$, $R^{17}$, $R^{18}$, $R^{20}$, $R^{21}$ and $R^{22}$ is understood as an alkyl residue with 1 to 30 carbon atoms. It is preferred that in particular the residues $R^{18}$, $R^{20}$, $R^{21}$ and $R^{22}$ are alkyl residues with 1 to 4 carbon atoms, in particular 1 to 2 carbon atoms. Concerning the residues $R^{15}$, $R^{16}$ and $R^{17}$, only one of the residues is preferably an alkyl residue with 8 to 30, preferably 10 to 20 carbon atoms. If the other residues in this group also represent an alkyl group, then they are preferably an alkyl residue with 1 to 4, in particular 1 to 2 carbon atoms. Alkyl residues with more than 2 carbon atoms can be straight-chained or branched. In addition the alkyl residue can also be unsaturated.

An alkyl group substituted by halogen in the definition of $R^{19}$, $R^{20}$, $R^{21}$ and $R^{22}$ is understood as an alkyl residue with 1 to 4 carbon atoms substituted by fluorine, chlorine, bromine or iodine. Alkyl residues with 1 to 2 carbon atoms substituted by fluorine are preferred. The trifluoromethyl residue is particularly preferred.

An alkoxy group in the definition of the residues $R^{15}$, $R^{16}$, $R^{17}$ is an alkoxy residue with 8 to 30, preferably 10 to 20 carbon atoms. The alkoxy residue can be straight-chained or branched, saturated or partially unsaturated.

Halogen in the definition of the residues $R^{20}$, $R^{21}$, $R^{22}$ can denote fluorine, chlorine, bromine or iodine; chlorine and bromine are preferred.

An alkylsulfonyl group in the definition of the residues $R^{19}$, $R^{20}$, $R^{21}$, $R^{22}$ denotes the group alkyl-$SO_2$—. In this connection the alkyl group represents an alkyl residue of 1 to 4, preferably 1 to 2 carbon atoms. The methylsulfonyl group is particularly preferred.

A sulfonamide group in the definition of the residue $R^{19}$ is understood as an unsubstituted amide (—$SO_2NH_2$) or an amide of a primary or secondary amine (—$SO_2NHR$ or —$SO_2NR_2$). Alkyl, aryl or aralkyl residues can be substituents of the amide (R). In the case of the amide of a secondary amine, the substituents (R) can be the same or different. An alkyl residue in this connection is understood as a residue with 1 to 4 carbon atoms. An aryl residue denotes an aromatic residue with 6 to 10 carbon atoms. Preferred aryl residues are phenyl or naphthyl residues. Aralkyl residues are those residues in which the aryl moeity is an aromatic residue with 6 to 10 carbon atoms and the alkyl moeity is a residue with 1 to 4 carbon atoms. The benzyl residue is a preferred aralkyl residue. The unsubstituted sulfonamide group (—$SO_2NH_2$) is particularly preferred.

Particularly preferred naphthol derivatives having the general formula IV are those in which one of the residues $R^{15}$, $R^{16}$ and $R^{17}$ represents an alkyl or alkoxy residue with 8 to 30, preferably 10 to 20 carbon atoms and the other residues of the aforementioned group denote hydrogen or an alkyl residue with 1 to 4, preferably 1 to 2 carbon atoms.

Particularly preferred naphthol derivatives are those in which $R^{15}$ represents an alkoxy group with 10 to 20 carbon atoms, $R^{16}$ and $R^{17}$ represent hydrogen and the other residues have the meaning stated for formula IV.

The compounds having the general formula IV can be produced analogous to known processes. Several variants of the process are possible for the production of naphthol derivatives having the general formula IV. Firstly naphthoquinones having the general formula V

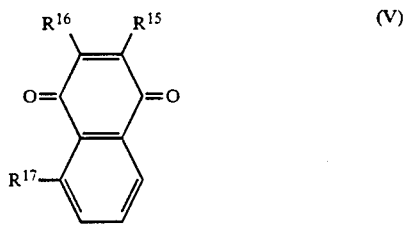

in which $R^{15}$, $R^{16}$ and $R^{17}$ have the meaning stated for the general formula IV can be reacted with a hydrazine having the general formula VI

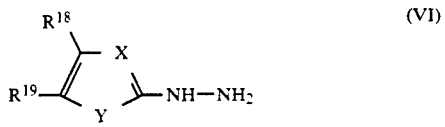

in which $R^{18}$, $R^{19}$, X and Y have the meaning stated for the general formula IV. This reaction can take place under the usual conditions for the formation of a hydrazone. The reaction preferably takes place under acidic conditions. The hydrazone per se is unstable and rearranges to form the desired naphthol having the general formula IV.

Another method for the production of the naphthol derivatives according to the present invention having the general formula IV starts with amines having the general formula VII

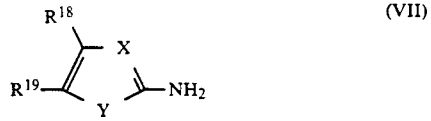

in which $R^{18}$, $R^{19}$, X and Y have the meanings stated for the formula IV. These amines are diazotized and the resulting diazonium salts are reacted in an azo coupling reaction with a naphthol having the general formula VIII.

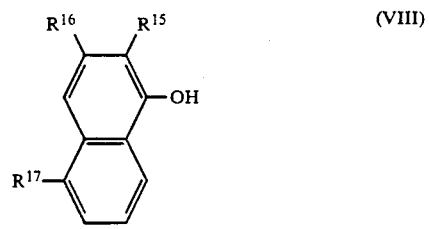

in which $R^{15}$, $R^{16}$ and $R^{17}$ have the meaning stated for the general formula IV.

The diazotization of the amines having the general formula VII can be carried out in the usual manner. It has proven to be advantageous to prepare concentrated mineral acids, for example concentrated sulphuric acid with a nitrite, preferably sodium nitrite and then to add the amine having the general formula VII while cooling to room temperature. A diazotization mixture which also contains glacial acetic acid apart from sodium nitrite and concentrated sulphuric acid has proven to be especially advantageous. The preferred volume ratio of sulphuric acid and glacial acetic acid is between 1:1 and 2:1. The ratio of nitrite and the amine to be diazotized having the general formula VII is usually equimolar.

After completion of the diazotization reaction the reaction mixture is processed aqueously. For this purpose the reaction mixture is preferably poured onto iced water. The diazonium salt per se is not isolated but is made to azo-couple with the naphthol having the general formula VIII in the aqueous processing solution. This is preferably carried out under weak acidic conditions. Naphthols having the general formula VIII are only very sparingly soluble in aqueous solutions. They are therefore applied in organic solvents. Chloroform is for example well suited as the organic solvent. In this way a diazonium salt solution which is present after the aqueous processing can be added to a solution of a naphthol having the general formula VIII in chloroform and glacial acetic acid, and an acetate can be added to buffer the pH value of the reaction medium. In most cases the naphthol derivatives which form having the general formula IV precipitate out of the reaction mixture. The product can then be recrystallized or purified chromatographically.

The pH indicators having the general formula IV are only slightly soluble in aqueous solutions but have good solubility in organic solvents.

According to the present invention the combination of 4-(2,6-dibromo-4-nitro-phenylazo)-2-octadecyloxynaphthol-1 as the pH indicator with 2,4,6,8-tetranitro-5-octadecyloxy-naphthol-1 as the acid has proven to be exceptionally useful.

The acids according to the present invention having the general formulae I, II and III, in combination with a pH indicator, are very well suited for increasing the measurement sensitivity in methods for the determination of an ion in an aqueous liquid according to the principle of the "heterogeneous pH reaction" as described in the introduction. They can be used in liquid-liquid extractions as described in principle by E. S. Hyman, Biophysical Society Abstracts, 1971, 72a as well as on "dry chemistry" test carriers which operate according to the principle of the heterogeneous pH reaction. Methods for the determination of an ion in an aqueous liquid which proceed according to the principle of the heterogeneous pH reaction have in common that the ion to be determined passes from the aqueous sample liquid into a phase which is immiscible with the aqueous liquid and as a result a pH indicator which is present there undergoes a change in colour which is used for the determination of the ion.

An agent according to the present invention for the determination of an ion in an aqueous liquid contains in an organic medium which is immiscible with water an ionophore which is responsible for transporting the ion to be determined from the aqueous liquid into the organic phase, in addition to the pH indicator soluble in an organic medium and an acid according to the present invention having the general formula I, II or III. In this connection "dry chemistry" agents for the determination of ions will be elucidated in more detail in the following. However, it is self evident to one skilled in the art that in principle the following statements apply in an analogous manner to liquid-liquid extractions and thus to non-test-carrier-bound test procedures.

Test carriers for the determination of ions which are based on the principle of the heterogeneous pH reaction are known from the state of the art as described in the introduction. They differ mainly in their embodiments i.e. how the organic phase is produced in a form which is appropriate for test carriers. In general, the organic phase consists of relatively non-volatile organic liquids which are immiscible with water and/or hydrophobic polymers. If both are present as a solid solution then they are referred to as plasticized plastics.

The acids having the general formula I, II or III according to the present invention can in principle be used in all of the test carriers for the determination of ions known from the state of the art which can be used to determine ions following the heterogeneous pH reaction. They have, however, proven to be particularly advantageous in test carriers in which they are present together with a naphthol derivative having the general formula IV in a film layer which contains a film resistant to liquids consisting of a hydrophobic polymer and solid inert particles dispersed therein. Such test carriers are described in DE-A-4015590.0. Examples of such test carriers are shown in FIG. 1 and 2.

Figure 2:
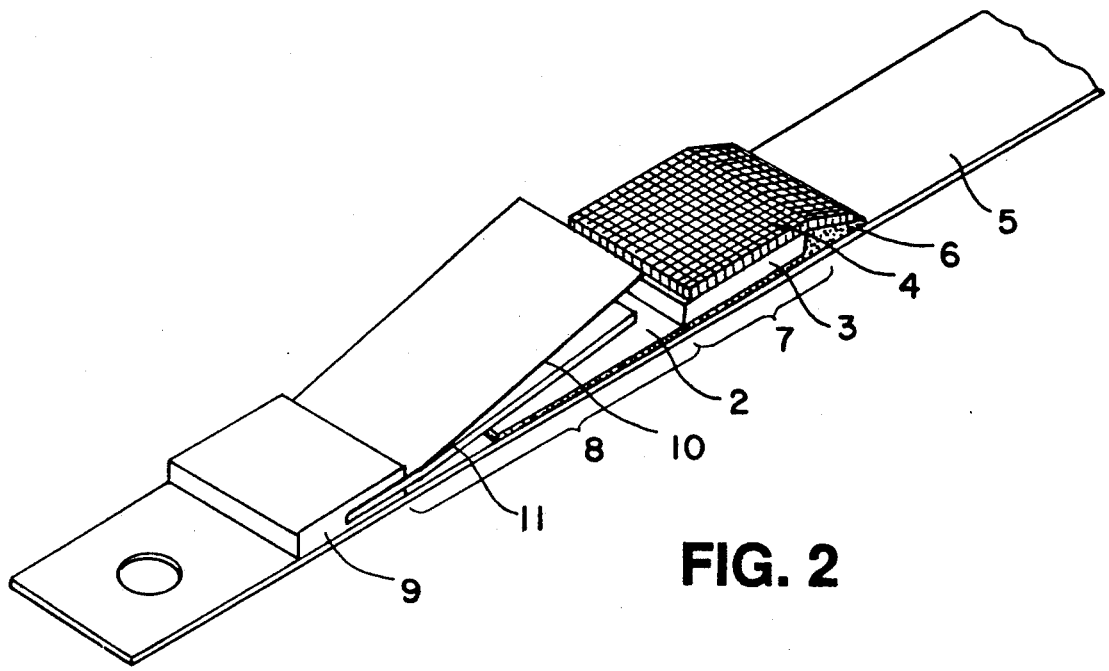
FIG. 2 shows a further test strip useful for the method according to the invention.

Two test carriers which are suitable for the determination of ions in blood are shown spatially in FIGS. 1 and 2. They allow the serum or plasma to be separated from whole blood and the determination of the ions of interest in the liquid obtained in this way to be carried out. The test carriers differ mainly in the location of the buffer substance within the test carrier. Details of the composition of the devices are as follows:

FIG. 1: A transport layer (2) which serves to transport the sample liquid from the sample application zone (7) into the test zone (8) is fixed onto an inert carrier foil (5), for example a plastic foil. In principle all materials are suitable as the transport layer (2) which are able to transport the liquid to be examined from the sample application zone (7) into the test zone (8) and which in this process do not alter it in such a way that the analysis becomes impaired. It is particularly preferable to use a glass fibre pad as the transport layer (2). A layer (3) for the separation of corpuscular components from the sample liquid is attached to the transport layer (2) and partially covers it. Basically any material can be used for this which enables corpuscular components from the sample liquid, in particular blood cells, and above all erythrocytes from blood, to be separated off and does not allow them to reach the test zone (8) in substantial amounts in order that they do not cause an interference in the test reaction there. In addition the separating layer (3) should not lead to a change in the sample liquid such that the concentration therein of the ion to be determined is changed and thus the result is falsified. Glass fibre pads, such as those described e.g. in EP-B-0 045 476, have proven to be particularly suitable for the separating layer (3). A protective layer (4) which is intended to prevent damage to the separating layer (3) during the sample application, for example with a pipette, is mounted over the separating layer (3). A net of inert material, for example of plastic, has proven to be of value for this. The protective layer (4) and separating layer (3) are fixed onto the inert carrier foil (5). This can for example be carried out by means of a strip of hot-melting adhesive (6). A carrier foil consisting of transparent plastic with a film layer (1) which contains the reagents necessary for carrying out the determination (also including a compound according to the present invention having the general formula I, II or III) is attached to one side of the transport layer (2). This is preferably effected by a glued joint (9) for example a strip of hot-melting adhesive. The film layer (1) is positioned so that it can be brought into contact with the transport layer (2) in such a way that liquid transfer is possible by pressing the transparent carrier foil down towards the inert carrier foil (5).

The film layer (1) contains a film which is resistant to liquids and consists of a hydrophobic polymer and particles dispersed therein. The hydrophobic polymer is impermeable to the liquid to be examined and it is also impermeable to the ions to be determined. The particles enable the sample liquid to penetrate into the film layer. The film layer (1) as such is impermeable to the liquid to be examined. A certain volume is merely taken up. Hydrophobic polymers which have proven to be advantageous are in particular copolymers of vinyl acetate. Particularly advantageous are copolymers of vinyl acetate with vinyl laurate or maleic acid dibutylester.

Solid, inert, inorganic or organic particles which are insoluble in the liquid to be examined and which have an oil absorption value of 80–200, preferably 100–170, can be used as the particles. In particular the different types of diatomaceous earths such as unbaked or natural kieselguhr, calcinated or baked kieselguhr, flow baked or activated kieselguhr have proven to be particularly advantageous for the film layer (1).

The oil absorption value is a well known parameter in the field of paints and coatings for particles which are for example used as fillers. It is a measure of the interaction between the particles and the medium in which they are dispersed. The oil absorption value is simple to determine. The determination is carried out according to DIN (German Industrial Standard) 53199. According to this norm the oil absorption value indicates the amount of linseed oil in g which is needed in order to process 100 g of the particles of interest into a coherent putty-like mass.

As a rule the particles used have an irregular shape. Their particle size is usually between 0.1 and 200 $\mu$m, preferably between 0.2 and 30 $\mu$m. A particular feature of the particles used according to the present invention is that they have cavities into which gases and wetting liquids can penetrate. A manifestation of this property is in particular the low bulk density of 50 to 250, preferably 80 to 180 g/l.

A ratio by weight of hydrophobic polymer to particle of 5:1 to 1:10 is practicable for the film layer (1). The ratio by weight is preferably 1:1 to 1:3. The optimal ratio by weight of hydrophobic polymer to particle is in any case dependent on the nature of the polymer used and the particles. If the hydrophobic polymer is a copolymer of vinyl acetate with vinyl laurate and/or maleic acid dibutylester and the particles are diatomaceous earths, the optimal ratio by weight is between 1:1.5 and 1:2.5.

Further necessary constituents of the film layer (1) are a difficultly volatile liquid which is immiscible with water, an ionophore, a pH indicator and an acid having the general formula I, II or III to increase the measurement sensitivity. These components are distributed homogeneously in the hydrophobic polymers.

A difficultly volatile liquid which is immiscible with water is understood as a plasticizer for plastics. Together with the polymer it serves as the actual organic phase for the method of determination of the ions according to the principle of the heterogeneous pH reaction. All possible commercial types of plasticizer, preferably sebacic acid, acrylic acid, phthalic acid and phosphoric acid esters as well as silicons, come into consideration as the plasticizer. For technical reasons concerning the processing, the very difficultly volatile Uvinul ®N539 (2,2-diphenyl-1-cyano-acrylic acid ethylhexylester) is particularly preferred.

The ratio by weight of hydrophobic polymer to difficultly volatile, hydrophobic, organic liquid in the test layer can be between about 5:1 to about 1:5, in particular between about 2:1 to about 1:2.

All substances which can complex the ions and which are specific for the ions to be determined and sufficiently soluble in a non-aqueous phase can be used as the ionophore. In this connection crown ethers, cryptands, podands and corresponding peptides of a cyclic or acyclic nature come into consideration. 2,3-naphtho-15-crown-5 has proven to be particularly advantageous for the determination of potassium. The natural ionophore valinomycin is especially preferred. For the determination of sodium, N,N'-dibenzyl-N'N-diphenyl-1,2-phenylene-dioxydiacetamide comes for example into consideration, for lithium, N,N'-diheptyl-5,5-dimethyl-N,N'-di(3-oxapentyl)-3,7-dioxanonane-diamide and for calcium, diethyl-N,N'-[(4R,5R)-4,5-dimethyl-1,8-dioxo-3,6-dioxa-octamethylene]-bis-(12-methylaminododecanoate). Naturally ionophores cannot be used which contain basic nitrogen atoms which are protonated by the acids according to the present invention and as a result lose their ability to form a complex which is selective for the ion to be determined. This applies particularly to cryptands. However, the overall majority of ionophores do not contain a nitrogen which can be protonated under the test conditions so that the universality of the invention is hardly limited.

In principle all pH indicators come into consideration which are adequately soluble in the organic phase and are so hydrophobic that they are not extracted from the organic phase with the aqueous sample to be investigated. For example tetrabromophenolphthaleinester or the indonaphthol derivatives described in EP-A-0 128 317 and EP-A-0 128 318 with alkyl side-chains of different length can be used. Chromoionophores can also be used. However, naphthol derivatives having the general formula IV as already characterized above are particularly well suited.

Since pH indicators are used and since they are sensitive to changes in pH, it is particularly advantageous to also incorporate a buffer in the film layer (1). In determination methods for ions which are based on a heterogeneous pH reaction, the pH of a buffer controls the transfer of the proton from the non-aqueous into the aqueous phase. In diagnostic agents for the determination of ions in body fluids the buffer substance is preferably chosen so that the pH can be adjusted to a value between 5-10, preferably between 7 to 8. In principle all the usual buffers come into consideration for this, provided they are soluble in water and do not contain ions which interfere with the test reaction. Buffers have proven to be suitable which are from the so-called Good buffer series such as e.g. N,N-bis-(hydroxyethyl)-aminoethanesulfonic acid (BES), 3-[N-trishydroxymethyl]-methylamino-hydroxypropanesulfonic acid (TAPSO) or N-hydroxyethylpiperazine-N-propanesulfonic acid (HEPPS).

If ionophores are used which are not sufficiently selective for the ion to be determined then water soluble complexing agents can be added which mask the interfering ions. Thus, for example a possible interference of a sodium test by calcium is prevented with ethylenediaminetetraacetate (EDTA).

In addition wetting agents can be used to improve the production of the films or the wetting of the films by the sample to be examined. Only those agents can be used for this which do not interfere with the test reaction. These are non-ionic and zwitterionic compounds. Of the non-ionic wetting agents polyethylene glycol ethers or esters, preferably Triton ® X100 have for example proven to be advantageous. n-decyl-N,N-dimethyl-3-ammonio-1-propanesulfonate (Zwittergent ® 3-10) can be used advantageously as a zwitterionic wetting agent.

In order to improve the consistency of the film layer (1), thickeners can be additionally used. Ethylcellulose has proven to be particularly advantageous for this. In addition to this hydrophilic thickening agents, such as for example hydroxyethyl- or hydroxypropylcellulose, can also be added to the film layer (1) for the aqueous phase which is present after wetting the film layer (1) with an aqueous liquid to be analyzed.

In order to produce a film layer (1), all components which, when the film layer is used for the determination of an ion in an aqueous liquid, in particular in a body fluid such as blood, plasma, serum or urine, should not be taken up in the aqueous phase but rather should remain in the organic phase i.e. the film layer (hydrophobic polymer; difficultly volatile liquid which is immiscible with water; ionophore; pH indicator; acid according to the present invention; if desired, thickener for improving the consistency of the film layer) are dissolved in a highly volatile to moderately volatile organic solvent. The particles are stirred into this solution and dispersed homogeneously therein. Afterwards the paste is spread out on a support with a doctor blade and dried. Of course other suitable methods of application can also be used such as roll coating, film casting or similar procedures. The dry film layer has a thickness of 20 to 500, preferably of 20 to 150 μm.

There are different ways of incorporating components (buffer; if desired complexing agent; if desired wetting agent; if desired thickener for changing the consistency of the aqueous phase) which are taken up into the aqueous phase when the aqueous sample liquid is applied to the film layer (1). One possibility is to coat the particles with the aforementioned components by evaporating, spray drying or freeze drying the particles together with an aqueous solution of the components. The particles coated in this way are then stirred into the organic solvent as described above. Another possibility is to first produce the film layer with untreated particles, then to re-coat with an aqueous solution of the aforementioned components and finally to dry.

FIG. 2 differs from FIG. 1 in that a layer (11), which contains those substances which are taken up into the aqueous phase during the determination reaction, is mounted between the film layer (10) and transport layer (2) via the glued joint (9) which is for example a strip of hot-melting adhesive. Such substances are in particular buffer substances. But also complexing agents, wetting agents or thickeners for changing the consistency of the aqueous phase can be incorporated into the additional layer (11) of the test carrier according to FIG. 2 instead of into the film layer (1) of the test carrier according to FIG. 1 or (10) of the test carrier according to FIG. 2. Absorptive materials which enable a liquid transfer to a further layer when this is brought into contact with them come into consideration as materials for the additional layer (11). Paper can be used particularly advantageously for this, but also nets made of an inert material such as plastic are possible.

In order to carry out the determination of an ion in blood by means of one of the test carriers shown in the figures, the sample is applied to the protective layer (4). The blood penetrates into the separation layer (3) and erythrocytes are separated from plasma or serum. The liquid obtained in this way is sucked into the test zone (8) by capillary forces. The aqueous phase in the transport layer (2) is brought into contact with film layer by pressure on the carrier foil with the film layer (1) or (10), liquid penetrates into the film layer and the determination reaction is triggered. The colour formed in the film layer which is a result of the reaction is observed visually or measured by reflectance photometry through the carrier foil of the film layer (1) or (10).

The following Table 1 indicates the advantageous and preferred percentages by weight of the components of a film layer (1) or (10):

TABLE 1

| Component of the film layer | Content of the film layer in % by weight | |
|---|---|---|
| | advantageous | preferred |
| polymer | 5–60 | 20–40 |
| difficultly volatile liquid which is immiscible with water | 5–70 | 20–40 |
| particles | 15–80 | 30–50 |
| ionophore | 0.05–5.0 | 0.2–1.0 |
| pH indicator | 0.05–5.0 | 0.2–0.7 |
| acid according to the invention | 0.005–5.0 | 0.02–0.7 |

If the buffer substance is applied in or onto the film layer (1) then this contains 5–30, preferably 10–20% by weight buffer. The substances which can be used, if desired, such as complexing agents, wetting agents or thickeners are in amounts—if they have been applied in or onto the film layer (1)—of 0.005 to 5, preferably 0.02 to 2% by weight of the film layer according to the present invention.

Figure 3:
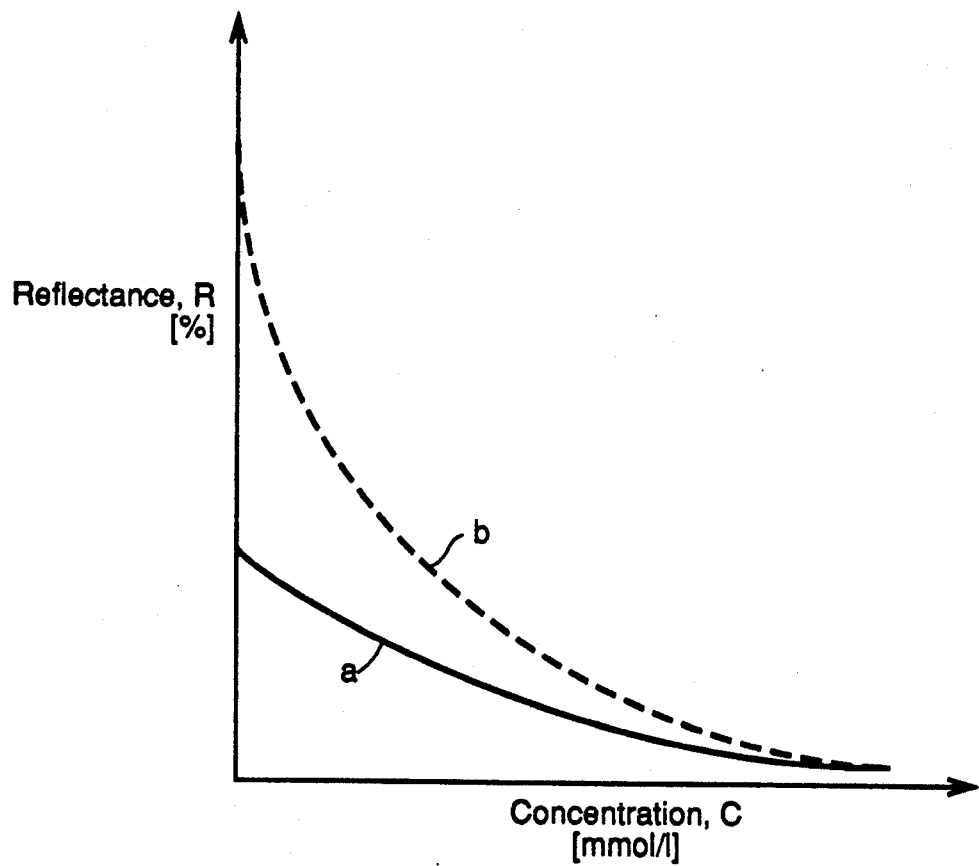
FIG. 3 show the relation between reflectance (R) and concentration (C) as determined with a test carrier for the determination of an ion in an aqueous liquid (a) according to the state of the art, and (b) according to the invention.

On test carriers, the colour change of the pH indicator as a measure for the amount of the ion to be determined can be evaluated visually. However, an evaluation by reflectance-photometric measurement can be carried out more accurately. As a generalization FIG. 3 shows a typical curve (a) which represents the relation between reflectance (R) and concentration (c) as determined with a test carrier for the determination of an ion in an aqueous liquid. While curve a shows the course which results without addition of an acid according to the present invention, curve b represents the relation between reflectance and concentration when an acid according to the present invention is also present in the organic phase apart from a pH indicator. Curve b (with acid) enables the exact determination of concentration since the slope of curve b is greater than that of a. It can therefore be seen from FIG. 3 (curve b) that by combining an acid having the general formula I, II or III with a pH indicator in a determination of ions which is based on the principle of the heterogeneous pH reaction, an increase in sensitivity compared to such tests without acid is possible.

Compounds having the general formula I'

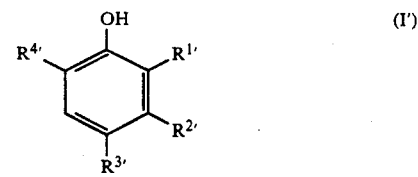

in which
R$^{2'}$ represents an alkyl or alkoxy residue and
R$^{1'}$, R$^{3'}$ and R$^{4'}$ are the same or different and each denotes a nitro group, halogen, a cyano group, an alkylsulfonyl group or an alkyl group substituted with halogen,
are novel and shall therefore also be a subject matter of the present invention.

The meanings of the definitions of the residues R$^{1'}$ to R$^{4'}$ correspond to those stated for the residues R$^1$ to R$^4$ of the general formula I.

The compounds can be produced analogous to known processes. In particular they can be prepared by aromatic substitution of corresponding starting compounds. Compounds having the general formula I,' in which R$^{1'}$, R$^{3'}$ and R$^{4'}$ are all the same and each denotes a nitro group, can for example be produced in such a way that first sulphuric acid and then nitric acid is added to a compound having the general formula IX

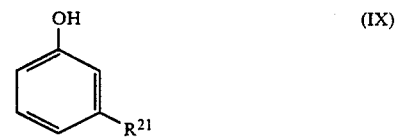

in which R$^{2'}$ represents an alkyl or alkoxy residue. Sulphonation of the starting substance is carried out first with concentrated sulphuric acid. If necessary the mixture has to be heated to 90° C. for this. In the subsequent nitration, in particular at temperatures below room temperature, preferably 0° to 25° C., introduction of the nitro groups takes place at the desired positions.

The compounds having the general formula II in which R$^7$ represents an alkyl, alkoxy or aralkyl residue, in particular an alkoxy residue and the other residues are the same or different and each denotes a nitro group, halogen, a cyano group, an alkylsulfonyl group or an alkyl group substituted with halogen or if R$^5$ and R$^6$ represent nitro groups, R$^8$ and R$^9$ can also denote hydrogen, are also novel. The meanings of the definitions of the residues R$^5$ to R$^9$ correspond to those initially stated.

The compounds having the general formula II can be produced analogous to known processes. In particular they can be made available (analogous to compounds having the general formula I') by aromatic substitution of corresponding starting compounds.

Compounds having the general formula II in which the residues R$^5$, R$^6$, R$^8$ and R$^9$ are the same and each denotes a nitro group can for example be produced in such a way that first sulphuric acid and then nitric acid are added to a compound having the general formula X

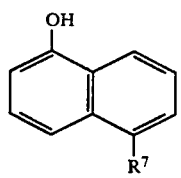

in which R⁷ represents an alkyl, alkoxy or aralkyl residue, in particular an alkoxy residue. First the starting compound is sulphonated, in particular with concentrated sulphuric acid. If necessary it must be heated to 50° C. for this. In the following nitration, in particular at temperatures below the maximum room temperature, preferably 0° to 10° C., the sulphonic acid groups are replaced and nitro groups are introduced.

If the compound having the general formula X is reacted directly with nitric acid, preferably in glacial acetic acid at room temperature, one obtains a compound having the general formula XI.

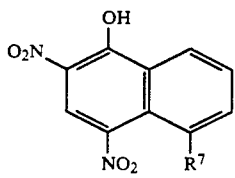

in which R⁷ has the same meaning as for compounds having the general formula X.

Novel compounds from the group of compounds having the general formula III are
[(2,3,5,6-tetrafluorophenyl)-hydrazono]propanedinitrile,
[(2-trifluoromethyl-4-nitrophenyl)-hydrazono]-propanedinitrile,
[(2-methanesulfonyl-4-nitrophenyl)-hydrazono]-propanedinitrile,
[(2,4-dinitro-6-cyanophenyl)-hydrazono]propanedinitrile
and [(3,5-di-{trifluoromethyl}phenyl)-hydrazono]-propanedinitrile They are also a subject matter of the present invention.

The listed compounds can be prepared by converting a corresponding aniline derivative (2,3,5,6-tetrafluoroaniline, 2-trifluoromethyl-4-nitroaniline, 2-methanesulfonyl-4-nitroaniline, 2,4-dinitro-6-cyanoaniline, 3,5-di-(trifluoromethyl)-aniline) into the corresponding diazonium salt and reacting with malodinitrile.

The diazotization of the aniline derivatives can take place in the usual manner. It has proven to be advantageous to prepare a concentrated mineral acid, for example concentrated sulphuric acid with a nitrite, preferable sodium nitrite, and to add the aniline derivative while cooling to room temperature. A diazotization mixture has proven to be especially advantageous which contains sodium nitrite and also glacial acetic acid apart from concentrated sulphuric acid. The preferred ratio by volume of sulphuric aicd and glacial acetic acid is between 1:1 and 2:1. The ratio of nitrite and aniline to be diazotized is usually equimolar.

The diazonium salt solution produced in this way is added to an aqueous, preferably acetate-buffered solution, of malodinitrile. The propanedinitrile derivatives formed usually precipitate from the reaction mixture and can then be purified by recrystallization or by chromatographic methods.

The invention is elucidated further in the following examples.

EXAMPLE 1

3-pentadecyl-2,4,6-trinitrophenol 67.5 g (0.2 mol) pentadecylphenol (90%) is added while stirring to 100 ml concentrated sulphuric acid in a 500 ml Erlenmeyer flask, heated to 90° C., whereby a dark-brown, highly viscous paste is formed which is difficult to stir and this is kept at 90° C. for 1 hour. In a separate 1 l three-neck flask 70 ml (ca. 1 mol) 65% nitric acid is cooled to 10° C. with the aid of an ice bath. The highly viscous sulfonation product obtained previously is added in small portions to the nitric acid during ca. 2 hours (whereby the viscous paste is kept liquid with a hair drier) while cooling with an ice bath in such a way that the temperature does not exceed 25° C. and in this process a beige-coloured paste which is difficult to stir is obtained which is stirred for a further hour at room temperature. Afterwards it is poured onto 500 g ice and while doing so a fine precipitate forms. The crude product obtained in this way can only be aspirated with difficulty which is why the total preparation is preferably centrifuged. After decanting off the supernatant liquid, this procedure is repeated twice after addition of water each time in order to remove adhering acid; the resulting precipitate is rinsed into a flask with 500 ml ethanol, dissolved by heating to 50° C. (in a water bath) and crystallized by placing it in an ice bath. After vigorous aspiration of the product one obtains 37.5 g (42.6% of the theoretical yield) of a weakly beige-coloured 3-pentadecyl-2,4,6-trinitrophenol which is slightly moist with ethanol, melting point 53°-56° C., TLC: silica gel 60, mobile solvent: ethyl acetate/methanol/-glacial acetic acid 90:5:5, R$_f$=0.8.

After drying the substance over diphosphorus pentoxide one obtains 35.75 g (40.1% of the theoretical yield) 3-pentadecyl-2,4,6-trinitrophenol, mp 59°-61° C.

EXAMPLE 2 a) 2,4,6,8-tetranitro-5-octadecyloxy-1-naphthol a) 5-octadecyloxy-1-naphthol 40 g (0.25 mol) 1,5-dihydroxynaphthalene (Janssen 99%) are suspended in 400 ml freshly distilled dimethylformamide in a 2 l three-neck flask with Claisen attachment, thermometer, calcium chloride tube and dropping funnel and 6 g (0.25 mol) 97% sodium hydride is added in small portions within 40 minutes. In this process the material becomes dissolved and shows a blue colour. Also hydrogen is formed and the temperature increases to 36° C. It is stirred for a further 30 minutes and 83.3 g (0.25 mol) 96% 1-octadecyl bromide are added dropwise to the 35° C. warm solution Within 10 minutes. Subsequently it is stirred again for 24 hours at room temperature. The crude product which is formed is aspirated vigorously and the residue is stirred with 600 ml water for 15 minutes. This procedure is repeated again and the filtration residue is washed so long with water (ca. 800 ml) until the filtrate is colourless. Afterwards the filter cake is dried at 40° C. in a drying cupboard over diphosphorus pentoxide. One obtains 98.6 g light beige crystals with a melting point of 76°-78° C.

For the further purification, the product is stirred three times with 750 ml each time of ethyl acetate, the undissolved constituents (40.8 g) light beige crystals are filtered off, the mother liquor is treated twice with charcoal and it is concentrated in a vacuum. One obtains 53.2 g (51.9% of the theoretical yield) beige coloured crystals with a melting point of 90°–92° C. This product is used directly for the production of the tetranitrated compound (Example 2b). TLC, silica gel 60 (merck), mobile solvent: toluol/methanol=50:1, $R_f=0.36$ b) 2.4.6.8-tetranitro-5-octadecyloxy-1-naphthol 1.2 l concentrated sulphuric acid are added to a 2 l three-neck flask with a large stirrer and thermometer, heated to 40° C. and 49.52 g (0.12 mol) 5-octadecyloxy-1-naphthol are added as rapidly as possible while stirring vigorously. After 5–10 minutes a viscous crystal pulp is formed and the temperature increases 2°–3° C. It is then stirred for a further 20 minutes without heating, then cooled to ca. 0° C. and nitrating acid (produced from 34.9 ml nitric acid (65%) which is added to 70 ml concentrated sulphuric acid within ca. 15 minutes while stirring and cooling to ca. 10°–20° C.) is added dropwise at 0°–5° C. within 30 minutes. In this process the reaction mixture becomes a grey-brown to red-brown colour. After stirring for a further 4 hours at 5°–10° C. it is poured onto ca. 5 kg ice and the crude product is extracted 3 times with 2 l ethyl acetate. Afterwards the ethyl acetate phases are combined, washed twice with 1 l water each time, the ethyl acetate phase is dried over sodium sulphate, aspirated and concentrated by evaporation. Ca. 80 g of a dark-brown resinous residue are obtained. This is purified by column chromatography. A column of 7.5 cm inside diameter, filling height ca. 110 cm, filling material: silica gel 60 (Merck) is used, mobile solvent: toluol/acetone 5:2. Main fraction $R_f=0.24$.

This crude substance is mixed again with ca. 400 ml mobile solvent and if not all is dissolved it is aspirated (the residue can block the column) and the filtrate is applied to the column and eluted in fractions. Fractions of 80 ml are taken. The forerun (colourless eluate) is ca. 2 l. The fractions containing the substance (30–140) are concentrated by evaporation. 21 g red-brown viscous paste is obtained which crystallizes out after standing for a long period. This product is dissolved in 42 ml acetone and the final product is precipitated by slow addition of the 5-fold amount of isohexane at room temperature. After stirring for five hours it is aspirated, the filter cake is washed with isohexane and dried in a vacuum over diphosphorus pentoxide and a molecular sieve at room temperature. 14.9 g (21% of the theoretical yield) of the desired tetranitro-octadecyloxy-naphthol is obtained, Fp 236°–238° C. (decomp.). TLC: silica gel 60 (Merck), mobile solvent: methylene chloride/methanol 8:1; $R_f=0.27$.

B) 2,4-dinitro-5-octadecyloxy-1-naphthol

A mixture of 3.78 g (2.5 ml) (0.06 Mol) nitric acid (density 1.52 g/cm$^3$) and 20 ml glacial acetic acid are added dropwise to a suspension of 8.25 g (0.02 Mol) 5-octadecyloxy-1-naphthol in 40 ml glacial acetic acid in a 250 ml three-neck flask with stirrer and thermometer while stirring vigorously at 20° to 30° C., it is stirred for a further 2 hours at 30° C., the precipitated crude product is suction-filtered over a glass filter and the residue is washed with a small volume of isohexane. After drying over diphosphorus pentoxide and a molecular sieve, 6.4 g brown crystals are obtained. This material is purified chromatographically on a silica gel 60 (E. Merck, Darmstadt, Germany) column (diameter 4.5 cm, filling height 80 cm). Mobile solvent: toluol/methanol=49:1. The appropriate fractions are concentrated by evaporation whereby 3.5 g orange-red crystals are obtained. After recrystallization from 50 ml n-heptane, 2.82 g (27.1% of the theoretical yield) of the desired dinitro compound are obtained as light-brown crystals, Fp 87°–89° C. TLC: silica gel 60 (E. Merck, Darmstadt, Germany), mobile solvent: toluol/methanol 30:1, $R_f=0.66$.

EXAMPLE 3

[(2,6-(dichloro)-4-(methylsulfonyl)-phenyl)hydrazono]-propanedinitrile 2.1 g (0.03 mol) sodium nitrite are dissolved in 30 ml concentrated sulphuric acid. In this process the temperature increases to 50° C. It is cooled to 20° C., 20 ml glacial acetic acid are added dropwise at 15°–20° C. and 7.2 g (0.03 mol) 2,6-dichloro-4-(methylsulfonyl)aniline are added in portions and it is stirred again for a further hour at 20° C.

1.98 g malodinitile are dissolved in 75 ml ethanol, a solution of 74 g sodium acetate-trihydrate in 35 ml water are added and the diazonium salt solution prepared above is added dropwise while stirring at 19° C. After stirring again for 1 hour, the crystallized product which forms is aspirated and the filtration residue is added to 300 ml water, extracted with methylene chloride, 200 ml trichloroethane are added, the extracts are dried over sodium sulphate and concentrated by evaporation to ca. 100 ml. Crystals which precipitate are aspirated and dried. 7.12 g (74.8% of the theoretical yield) are obtained as sand-coloured crystals, mp 165°–168° C.

EXAMPLE 4

The following propanedinitrile hydrazones are prepared analogous to Example 3 a) [(2,3,5,6-tetrafluorophenyl)-hydrazono]propanedinitrile, Fp 103°–106° C., from 2,3,5,6-tetrafluoroaniline b) [(4-nitrophenyl)-hydrazono]propanedinitrile, mp 220° C. from p-nitroaniline (Lithgoe, Todd, Topham, Chem. Soc. 1944, 315)

c) [(2,4-dinitrophenyl)-hydrazono]propanedinitrile, TLC, silica gel 60 (Merck), mobile solvent: methylene chloride/methanol=98:2, $R_f=0.28$ from 2,4-dinitroaniline (NL-A-6411189)

d) [(2,4-dichlorophenyl)-hydrazono]propanedinitrile, mp 114°–116° C. from 2,4-dichloroaniline (NL-A-6411189)

e) [(3,5-dichlorophenyl)-hydrazono]propanedinitrile, mp 200° C. (decomp.), from 3,5-dichloroaniline (NL-A-6411189)

f) [(3,5-dichloro-2,4,6-tribromophenyl)-hydrazono]-propanedinitrile, mp 193°–196° C., from 3,5-dichloro-2,4,6-tribromoaniline (NL-A-6411189)

g) [(2,4-dichloro-6-bromophenyl)-hydrazono]-propanedinitrile, mp 134°–136° C. from 2,4-dichloro-6-bromoaniline (Eur. J. Med. Chem. Clin. Therap. 12, 361 [1977])

h) [2,4,6-trichlorophenyl)-hydrazono]propanedinitrile, mp 225°–226° C., from 2,4,6-trichloroaniline (Eur. J. Med. Chem. Clin. Therap. 12, 361 [1977])

i) [(2-trifluoromethyl-4-nitrophenyl)hydrazono]-propanedinitrile, mp 245° C., from 2-trifluoromethyl-4-nitroaniline j) [(2,4,6-tribromophenyl)-hydrazono]propanedinitrile, mp 153° C., from 2,4,6-tribromoaniline (Eur. J. Med. Chem. Clin. Therap. 12, 361 [1977])

k) [(2-methanesulfonyl-4-nitrophenyl)hydrazono]-propanedinitrile, mp 220° C., from 2-methanesulfonyl-4-nitroaniline l) [(2,4-dinitro-6-cyanophenyl)hydrazono]propanedinitrile, TLC, silical gel 60 (Merck), mobile solvent: toluol/methyl ethyl ketone 1:2, $R_f$=0.50, from 2,4-dinitro-6-cyanoaniline (W. Thiel et al., J. Pract. Chem. 328, 499 (1986))

m) [(3,5-di-{trifluoromethyl}phenyl)hydrazono]-propanedinitrile, mp 150°–151° C., from 3,5-di-(trifluoromethyl)-aniline

EXAMPLE 5

4-[2,6-dibromo-4-nitrophenyl)azo]-2-otadecyloxy-1-naphthol a) 2-octadecyloxynaphthalene 172.8 g (1.2 mol) 2-naphthol (98%) is added to a solution of 48 g (1.2 mol) sodium hydroxide (99%) in 1 l ethanol in a 4 l three-neck flask with stirrer, cooler and thermometer, after it has dissolved 417 g (1.25 mol) n-octadecylbromide are added and the reaction mixture is heated for 14 hours under reflux. After addition of a further 1 l ethanol the hot solution is aspirated over a Seitz filter to remove inorganic material and the weakly pink coloured filtrate is brought to crystallization by placing it in an ice bath for 30 minutes. After aspiration of the almost colourless crystals, the filter cake is washed in portions with ca. 700 ml ethanol and after drying over diphosphorus pentoxide 371.9 g (93.7% of the theoretical yield) 2-octadecyloxynaphthalene are obtained as colourless crystals, Fp 64°–68° C.

TLC: silica gel 60 (Merck), mobile solvent: n-heptane/methyl ethyl ketone 2:1, $R_f$=0.34 b) 2-octadecyloxy-1-naphthol 594 g (1.5 mol) 2-octadecyloxynaphthalene and 397 g (0.75 mol) lead tetraacetate are added to a mixture of 3 l glacial acetic acid and 600 ml acetic anhydride in a 10 l three-neck flask with stirrer, Claisen attachment, thermometer and cooler with a calcium chloride tube and it is heated to 55° C. Over a period of 4 days a further 400 g lead tetraacetate are added in portions (each of 100 g) at intervals of 24 hours while stirring. Afterwards the yellow solution which is formed is cooled to room temperature, stirred again for 30 minutes after addition of 1.5 l water, the crystal slurry which forms is aspirated and washed in portions with 2 l water. The wet crude product is dissolved in 4 l toluol and shaken three times with 1 l portions of water, three times with 1 l saturated sodium hydrogen carbonate solution and then again three times with 1 l water. After drying the toluol phase over sodium sulphate, aspiration and concentration by evaporation, 635 g brown crude product are obtained which is purified chromatographically as follows: the crystallizate obtained is dissolved in a mixture of 1.3 l toluol/isohexane 5:2 and the solution is applied to a silica gel 60 (Merck) column, inside diameter 11.5 cm, filling height 1.2 m. Toluol/isohexane 5:2 is used as the mobile solvent and fractions of ca. 300 ml are taken. Fractions 9–52 are combined and concentrated by evaporation until constancy of weight. One obtains 324.2 g 2-octadecyloxy-1-naphthol acetate, Fp 67°–68° C. This is dissolved without further purification in 1.8 l methanol while heating and cooled to 20° C. 93 ml concentrated sulphuric acid are added dropwise to the suspension which forms within 15 minutes without cooling and while stirring, whereby the temperature increases to 35° C. Subsequently it is heated for 2 hours under reflux, then cooled with an ice bath and stirred for a further 30 minutes while cooling on ice. The crystals which form are aspirated, washed with 150 ml ice-cold methanol and dried at 35° C. in a drying cupboard over diphosphorus pentoxide. One obtains 294.4 g (47.5% of the theoretical yield) 2-octadecyloxy-1-naphthol, colourless crystals, Fp 58°–59° C.

c) 4-[(2,6-dibromo-4-nitrophenyl)azo]-2-octadecyloxy-1-naphthol 22.7 g (0.33 mol) sodium nitrite are fed into 300 ml concentrated sulphuric acid in a 2 l three-neck flask with stirrer, Claisen attachment and thermometer during 10–15 minutes while stirring whereby the temperature of the reaction solution is allowed to increase to 35° C. It is then cooled to 20° C. and 230 ml glacial acetic acid are added dropwise in ca. 15–20 minutes in such a way that the temperature is held at 20°–25° C. while cooling on ice. Afterwards 97.6 ml (0.33 mol) 2,6-dibromo-4-nitroaniline (Riedel de Haen [99% GC] are added in portions during 10 minutes while cooling occasionally whereby the temperature is kept at 19°–21° C. and it is stirred again for a further 3 hours. Afterwards it is poured onto 3.5 l iced water and the diazonium salt solution which forms is added rapidly to a solution of 124 g (0.3 mol) 2-octadecyloxy-1-naphthol in a mixture of 3 l glacial acetic acid and 300 ml chloroform with addition of 180 g (1.33 mol) sodium acetatetrihydrate. (In the production of the solution of the naphthol ether care must be taken that after it has been fed into glacial acetic acid/chloroform with addition of sodium acetate it is again cooled down to 20° C. after a temperature increase to ca. 45° C.) After stirring for 3 hours in the ice bath the crystallizate which is formed is aspirated, the residue is washed three times with 500 ml water each time and dried in a drying cupboard at 40° C. The crude product—295.5 g light brown crystals—is purified chromatographically. The azo compound is dissolved in 1 l toluol/methylene chloride 2:5 and applied to a silica gel 60 (Merck) column with an inside diameter of 11.5 cm, filling height of 1.2 m and eluted with toluol/methylene chloride 2:5. Fractions of ca. 70 ml are taken. The fractions 57–173 are combined and concentrated by evaporation. One obtains 134.2 g brown crystals. These are dissolved in 480 ml toluol at 80° C., cooled to 65° C. and 800 ml isohexane are added while stirring vigorously. It is allowed to cool to 20° C. while stirring, placed overnight in a refrigerator, the crystals which form are aspirated and the filter cake is washed twice with 300 ml ice-cold toluol/isohexane 1:1.3 and subsequently with 300 ml isohexane. Afterwards it is dried in a drying cupboard at 40° C. over diphosphorus pentoxide until constancy of weight. One obtains 119.9 g (55.5% of the theoretical yield) azo compound, light brown crystals, Fp 102°–103° C. TLC, silica gel 60 (Merck), mobile solvent: toluol/methylene chloride 2:5, $R_f$=0.37.

EXAMPLE 6

4-[(2-bromo-4-nitro-6-trifluoromethylphenyl)-azo]-2-octadecyloxy-1-naphthol

This compound is produced analogously to Example 5 from 2-bromo-4-nitro-6-trifluoromethyl aniline (M. Hauptschein et al., J. Amer. Chem. Soc. 76, 1051 (1954)), mp 84° C.

EXAMPLE 7 a) 2-(3,7,11,15-tetramethyl-2-hexadecenyl)-3-methyl-4-(2,4-dinitrophenyl)azo]-1-naphthol 19.8 g (0.1 mol) 2,4-dinitrophenylhydrazine in 400 ml ethanol are suspended in a 2 l three-neck flask with stirrer, cooler and thermometer with addition of 9 ml (0.11 mol) concentrated hydrochloric acid and 45 g (0.1 mol) vitamin $K_1$ [2-methyl-3-(3,7,11,15-tetramethyl-2-hexadecyl)-1,4-naphthoquinone] are added, it is stirred for 15 minutes at room temperature, then heated for 4 hours under reflux. Afterwards it is concentrated in a vacuum. 64 g red-brown viscous paste is obtained. This is purified chromatographically on a silica gel 60 (Merck) column, inside diameter 10.5 cm, filling height 110 cm with methylene chloride/n-heptane as mobile solvent. Because of the sparing solubility of the reaction product the crude product is dissolved in 350 ml of the mobile solvent, insoluble constituents are filtered off over a Seitz filter and it is applied to the silica gel column. The appropriate fractions are combined, concentrated in a vacuum and the orange-coloured wax-like product is recrystallized twice from 100 ml n-propanol/ligroin 1:1 each time, the residue is washed twice With 20 ml n-propanol/ligroin 1:1 and dried until constancy of weight. 19.41 g (31% of the theoretical yield) orange-coloured, wax-like, TLC-uniform crystals are obtained, mp 110° C.

The following can be produced in an analogous manner:

b) 2-(3,7,11,15-tetramethyl-2-hexadecenyl)-3-methyl-4-(4-nitrophenyl)azo]-1-naphthol TLC, silica gel 60 (Merck), mobile solvent: toluol/methanol=50:1; $R_f=0.22$ from 4-nitrophenylhydrazine

EXAMPLE 8

General Instructions for the Production of Test Carriers

For the production of a test carrier according to FIG. 1, transparent polyester foil (200 μm thick) is coated with the mixtures mentioned in the following Examples and dried. The coated foil is cut into 15 mm wide strips and glued as layer (1) with hot-melting adhesive longitudinally onto 150 mm wide white polyester foil (5). Strips of glass fibre fleece with an area weight of 30 g/m² as transport layer (2), of glass fibre fleece with an area weight of 60 g/m² as separation layer (3) and of polyamide fabric as protective layer (4) are also glued longitudinally onto this white polyester foil so that after cross-cutting 6 mm wide test strips according to FIG. 1 are formed.

Test carriers according to FIG. 2 are produced analogously. The layer (11) consists of filter paper which is impregnated with a buffer substance.

The film layer or test carrier according to the present invention are used in such a way that 30 μl of the sample to be examined is applied to the polyamide fabric (4) and the test carrier is then inserted into the commercial reflectance photometer Reflotron® (Boehringer Mannheim GmbH, Mannheim, Federal Republic of Germany). The liquid penetrates into the glass fibre pad (3), where in the case of whole blood the erythrocytes are separated, and reaches the glass fibre zone (8) which serves as the transport layer. In the reflectance photometer the film under the flap (1) or (10) is brought into contact with the liquid in the transport layer (2) by pressure on the flap and the colour formed is measured by reflectance photometry at 642 nm and 37° C.

EXAMPLE 9

A mixture of the following composition is produced and applied with a wet film thickness of 300 μm to a transparent polyester foil and dried:

| | |
|---|---|
| Vinyl acetate-vinyl laurate-copolymer (Vinnapas ®B 500/20 VL, Wacker Chemie, Munich, Germany) | 13.11 g |
| 2,2-diphenyl-1-cyano-acrylic acid-ethylhexylester (Uvinul ®N539, BASF, Ludwigshafen, Germany) | 16.04 g |
| 4-[(2,6-dibromo-4-nitrophenyl)azo]-2-octadecyloxy-1-naphthol (produced according to Example 5) | 0.173 g |
| 2,4,6,8-tetranitro-5-octadecyloxy-naphthol-1 (Example 2) | 0.0456 g |
| Valinomycin | 0.2673 g |
| Diatomaceous earth (Celatom ® MW 25, Eagle-Picher, Cincinatti, USA) | 25.13 g |
| Butyl acetate | 45.17 g |

A second layer of the following composition having a wet film thickness of 150 μm is applied to this layer and dried in the same way:

| | |
|---|---|
| Hydroxyethyl cellulose (Natrosol ® 250G, Hercules Inc., Willmington, Delaware, USA) 2% in water | 24 g |
| N,N-bis-(hydroxyethyl)-aminoethane-sulfonic acid(BES) | 8.2 g |
| Ethanol | 42 ml |
| adjusted to pH 7.5 with LiOH. | |

In addition a test film is produced having the same composition but without 2,4,6,8-tetranitro-5-octadecyloxy-naphthol-1.

Test strips according to FIG. 1 are produced from the coated foils as described in Example 8 and measured. The measurement takes place 60 seconds after contact of the sample with the reagent film.

When sera are used with different contents of potassium the following dependence of the reflectance (% R) on the potassium content is found:

TABLE 2

| | Reflectance [% R] | |
|---|---|---|
| Potassium content [mmol potassium/l] | with 2,4,6,8-tetranitro-5-octadecyloxy-naphthol-1 | without |
| 0.24 | 62.0 | 34.4 |
| 1.09 | 55.8 | 28.5 |
| 1.87 | 50.3 | 24.8 |
| 3.18 | 43.2 | 21.2 |
| 4.15 | 38.3 | 19.3 |
| 6.08 | 32.3 | 16.8 |
| 8.10 | 27.5 | 15.0 |
| 10.22 | 24.0 | 13.8 |
| 12.10 | 21.5 | 12.9 |

It is apparent that in the diagnostically important range of ca. 2–6 mmol/l potassium a difference in the measured values of ca. 18% R can be achieved with the acid according to the present invention whereas without this acid it is only ca. 8% R.

EXAMPLE 10

A mixture of the following composition is produced and applied with a wet film thickness of 300 μm to a transparent polyester foil and dried:

| | |
|---|---|
| Vinyl acetate-maleic acid dibutyl ester copolymer (Mowilith ®35/73, Hoechst, Frankfurt, Germany) | 14.7 g |
| 2,2-diphenyl-1-cyano-acrylic acid-ethylhexylester (Uvinul ®N539, BASF, Ludwigshafen, Germany) | 18.4 g |
| 4-[(2,6-dibromo-4-nitrophenyl)azo]-2-octadecyloxy-1-naphthol (produced according to Example 5) | 0.130 g |
| Bis-(2-hydroxy-3,5,6-trichlorophenyl)-methane (Hexachlorophene, Aldrich, Steinheim, Germany) | 0.029 g |
| Valinomycin | 0.600 g |
| Diatomaceous earth (Celatom ® MW 25, Eagle-Picher, Cincinatti, USA) | 28.2 g |
| Butyl acetate | 50.7 g |

A second layer of the following composition having a wet film thickness of 150 μm is applied to this layer and dried in the same way:

| | |
|---|---|
| Hydroxyethyl cellulose (Natrosol ® 250G, Hercules Inc., Willmington, Delaware, USA) 4% in water | 41.5 g |
| N,N-bis-(hydroxyethyl)-aminoethane-sulfonic acid (BES) | 8.5 g |
| Ethanol adjusted to pH 7.8 with LiOH. | 64 ml |

In addition a test film is produced having the same composition but without hexachlorophene.

Test strips according to FIG. 1 are produced from the coated foils as described in Example 8 and measured. The measurement takes place 60 seconds after contact of the sample with the reagent film.

When sera are used with different contents of potassium the following dependence of the reflectance (% R) on the potassium content is found:

TABLE 3

| Potassium content [mmol potassium/l] | Reflectance [% R] | |
|---|---|---|
| | with hexachlorophene | without hexachlorophene |
| 1.00 | 54.2 | 33.4 |
| 1.98 | 47.8 | 28.5 |
| 2.99 | 41.6 | 25.1 |
| 4.12 | 37.4 | 22.7 |
| 6.00 | 30.8 | 19.3 |
| 8.04 | 26.4 | 17.1 |
| 10.12 | 23.2 | 15.4 |
| 11.98 | 21.7 | 14.3 |

It is apparent that in the diagnostically important measured values of ca. 2-6 mmol/l potassium a difference in the measured values of ca. 17% R can be achieved with the acid according to the present invention whereas without this acid it is only ca. 9% R.

EXAMPLE 11

A mixture of the following composition is produced and applied with a wet film thickness of 300 μm to a transparent polyester foil and dried:

| | |
|---|---|
| Vinyl acetate-vinyl laurate copolymer (Vinnapas ®B 500/20 VL, Wacker Chemie, Munich, Germany) | 19.6 g |
| 2,2-diphenyl-1-cyano-acrylic acid-ethylhexylester (Uvinul ®N539, BASF, Ludwigshafen, Germany) | 24.0 g |
| 4-[(2-bromo-4-nitro-6-trifluoromethylphenyl)azo]-2-octadecyloxy-1-naphthol (produced according to Example 6) | 0.071 g |
| [(2,4-dinitrophenyl)-hydrazono]propanedinitrile (Example 4 c) | 0.052 g |
| Valinomycin | 0.30 g |
| Diatomaceous earth (Celatom ® MW 25, | 37.5 g |

-continued

| | |
|---|---|
| Eagle-Picher, Cincinatti, USA) | |
| m-Xylol | 67.4 g |

In addition a test film is produced having the same composition but without [(2,4-dinitrophenyl)hydrazono]propanedinitrile.

Long fibre paper 6776 (Schöller and Hösch, Gernsbach, Germany) is impregnated with the following solution and dried:

| | |
|---|---|
| N,N-bis-(hydroxyethyl)-aminoethane-sulfonic acid (BES) | 8.5 g |
| n-octylglucoside | 0.1 g |
| water, distilled adjusted to pH 7.5 with LiOH. | 91.5 ml |

Test strips according to FIG. 2 are produced from the coated foils (10) and the buffer paper (11) as described in Example 8 and measured. The measurement takes place 60 seconds after contact of the sample with the reagent film.

When sera are used With different Contents of potassium the following dependence of the reflectance (% R) on the potassium content is found:

TABLE 4

| Potassium content [mmol potassium/l] | Reflectance [% R] | |
|---|---|---|
| | with [(2,4-dinitrophenyl)-hydrazono]-propanedinitrile | without [(2,4-dinitrophenyl)-hydrazono]-propanedinitrile |
| 0.08 | 63.6 | 33.9 |
| 1.01 | 57.0 | 24.8 |
| 1.98 | 46.3 | 21.2 |
| 3.10 | 37.6 | 18.9 |
| 4.08 | 31.0 | 17.6 |
| 6.08 | 25.0 | 15.7 |
| 8.05 | 22.0 | 14.5 |
| 9.90 | 20.0 | 13.6 |

It is apparent that in the diagnostically important range of ca. 2-6 mmol/l potassium a difference in the measured values of ca. 21% R can be achieved with the acid according to the present invention whereas without this acid it is only ca. 5.5% R.

Test strips with a similar difference in reflectance are obtained when using the 3,5-di-trifluoromethylphenylhydrazone of mesoxalic acid dinitrile (Example 4 m) instead of the 2,4-dinitrophenylhydrazone.

EXAMPLE 12

A mixture of the following composition is produced and applied with a wet film thickness of 300 μm to a transparent polyester foil and dried:

| | |
|---|---|
| Vinyl acetate-vinyl laurate copolymer (Vinnapas ®B 500/20 VL, Wacker Chemie, Munich, Germany) | 5.9 g |
| 2,2-diphenyl-1-cyano-acrylic acid-ethylhexylester (Uvinul ®N539, BASF, Ludwigshafen, Germany) | 7.2 g |
| 2-(3,7,11,15-tetramethyl-2-hexadecenyl)-3-methyl-4-(4-nitrophenyl)azo]-1-naphthol (produced according to Example 7) | 0.032 g |
| 2,4,6-trinitro-3-pentadecyl-phenol (Example 1) | 0.020 g |
| Valinomycin | 0.120 g |
| Diatomaceous earth (Celatom ® MW 25, Eagle-Picher, Cincinatti, USA) | 11.3 g |
| Butyl acetate | 20.3 g |

A second layer of the following composition having a wet film thickness of 150 μm is applied to the layer and dried in the same way:

| | |
|---|---|
| Hydroxyethyl cellulose (Natrosol ®250G, Hercules Inc., Willmington, Delaware, USA) 2% in water | 150 g |
| Boric acid | 4.64 g |
| Ethanol | 198 ml |
| adjusted to pH 9.5 with LiOH. | |

In addition a test film is produced having the same composition but without 2,4,6-trinitro-3-pentadecyl-phenol.

Test strips according to FIG. 1 are produced from the coated foils as described in Example 8 and measured. The measurement takes place 60 seconds after contact of the sample with the reagent film.

When sera are used with different contents of potassium the following reflectance values are measured:

TABLE 5

| | Reflectance [% R] | |
|---|---|---|
| Potassium content [mmol potassium/l] | with 2,4,6-trinito-3-pentadecyl-phenol | without 2,4,6-trinito-3-pentadecyl-phenol |
| 0.24 | 66.5 | 54.3 |
| 1.09 | 62.8 | 48.4 |
| 1.87 | 59.9 | 44.2 |
| 3.18 | 55.8 | 39.8 |
| 4.15 | 52.7 | 37.7 |
| 6.08 | 47.8 | 33.9 |
| 8.10 | 43.6 | 31.3 |
| 10.22 | 40.1 | 29.0 |
| 12.10 | 37.4 | 27.1 |

It is apparent that in the diagnostically important range of ca. 2–6 mmol/l potassium a difference in the measured values of ca. 12% R can be achieved with the acid according to the present invention whereas without this acid it is only ca. 10% R.

Similar results with a measurement difference of ca. 11.5% are obtained with test strips with an analogous composition which contain equimolar amounts of 2,4-dinitro-5-octadecyloxy-naphthol-1 (produced according to Example 2B) instead of 2,4,6-trinitro-3-pentadecyl-phenol.

We claim:

1. Method for determining an ion in an aqueous sample comprising contacting said aqueous sample with a water immiscible composition comprising:
   (i) an ionophore which complexes with said ion
   (ii) a pH indicator which undergoes a color change when releasing a hydrogen ion, and
   (iii) a compound selected from the group consisting of:

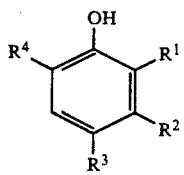
(a)

wherein at least one of the group consisting of $R^1$, $R^2$, $R^3$ and $R^4$ is an alkyl, alkoxy, or aralkyl group, the remaining members of the group consisting of $R^1$, $R^2$, $R^3$ and $R^4$ are the same or different and are each a member selected from the group consisting of a nitro group, a halogen, a cyano group, an alkylsulfonyl group and a halogen substituted alkyl group;

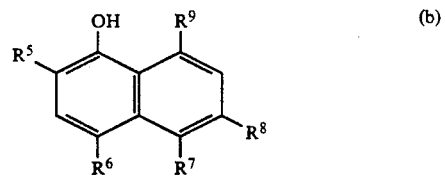
(b)

wherein at least one of the group consisting of $R^5$, $R^6$, $R^7$, $R^8$ and $R^9$ is an alkyl group, an alkoxy group or an aralkyl group, the rest of the group consisting of $R^5$, $R^6$, $R^7$, $R^8$ and $R^9$ are the same or different and are selected from the group consisting of a nitro group, a halogen, a cyano group, an alkylsulfonyl group and a halogen substituted alkyl group, with the proviso that if $R^5$ and $R^6$ are nitro groups, $R^8$ and $R^9$ can be hydrogen, and

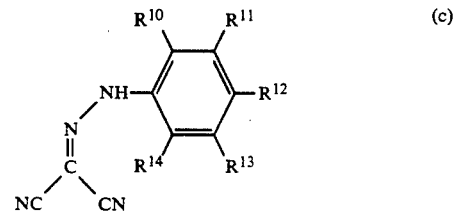
(c)

wherein $R^{10}$, $R^{11}$, $R^{12}$, $R^{13}$ and $R^{14}$ are the same or different and are selected from the group consisting of hydrogen, halogen, a nitro group, a cyano group, an alkylsulfonyl group and a halogen substituted group, under conditions favoring complexing of said ion with said ionophore and causing release of a $H^+$ ion from said pH indicator and measuring color change of said pH indicator as a determination of said ion.

2. Method of claim 1, wherein said pH indicator has formula

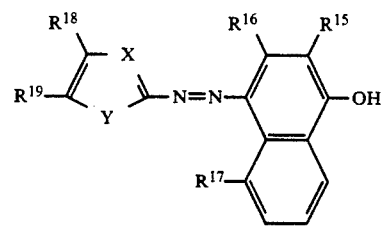

wherein
$R^{15}$, $R^{16}$ and $R^{17}$ are the same or different and are selected from the group consisting of hydrogen, an alkyl group and an alkoxy group, with the proviso that at least one of $R^{15}$, $R^{16}$ and $R^{17}$ is a $C_8$–$C_{30}$ alkyl group or $C_8$–$C_{30}$ alkoxy group,
$R^{18}$ is hydrogen or an alkyl group,
$R^{19}$ is a nitro group, a halogen substituted alkyl group, a cyano group, a sulfonamido group or an alkylsulfonyl group,
X is nitrogen or $CR^{20}$
Y is sulphur or $CR^{21}=CR^{22}$
wherein $R^{20}$, $R^{21}$ and $R^{22}$ are the same or different and are selected from the group consisting of a hydrogen, a halogen, a nitro group, a cyano group, an alkyl group, a halogen substituted alkyl group and an alkylsulfonyl group.

3. Composition useful in determining an ion in an aqueous sample, comprising a water immiscible medium containing:
(i) an ionophore,
(ii) a pH indicator, and
(iii) a compound selected from the group consisting of:

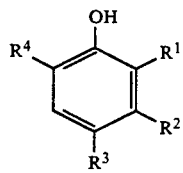
(a)

wherein at least one of the group consisting of $R^1$, $R^2$, $R^3$ and $R^4$ is an alkyl, alkoxy, or aralkyl group, the remaining members of the group consisting of $R^1$, $R^2$, $R^3$ and $R^4$ are the same or different and are each a member selected from the group consisting of a nitro group, a halogen, a cyano group, an alkylsulfonyl group and a halogen substituted alkyl group;

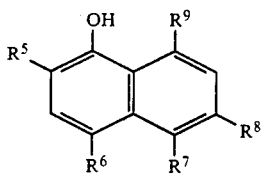
(b)

wherein at least one of the group consisting of $R^5$, $R^6$, $R^7$, $R^8$ and $R^9$ is an alkyl group, an alkoxy group or an aralkyl group,
the rest of the group consisting of $R^5$, $R^6$, $R^7$, $R^8$ and $R^9$ are the same or different and are selected from the group consisting of a nitro group, a halogen, a cyano group, an alkylsulfonyl group and a halogen substituted alkyl group, with the proviso that if $R^5$ and $R^6$ are nitro groups, $R^8$ and $R^9$ can be hydrogen, and

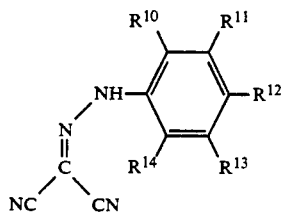
(c)

wherein $R^{10}$, $R^{11}$, $R^{12}$, $R^{13}$ and $R^{14}$ are the same or different and are selected from the group consisting of hydrogen, halogen, a nitro group, a cyano group, an alkylsulfonyl group and a halogen substituted group.

4. Composition of claim 3, wherein said pH indicator is a compound of formula:

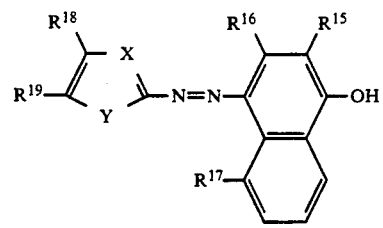

wherein
$R^{15}$, $R^{16}$ and $R^{17}$ are the same or different and are selected from the group consisting of hydrogen, an alkyl group and an alkoxy group, with the proviso that at least one of $R^{15}$, $R^{16}$ and $R^{17}$ is a $C_8$–$C_{30}$ alkyl group or $C_8$–$C_{30}$ alkoxy group,
$R^{18}$ is hydrogen or an alkyl group,
$R^{19}$ is a nitro group, a halogen substituted alkyl group, a cyano group, a sulfonamido group or an alkylsulfonyl group,
X is nitrogen or $CR^{20}$
Y is sulphur or $CR^{21}=CR^{22}$
wherein $R^{20}$, $R^{21}$ and $R^{22}$ are the same or different and are selected from the group consisting of a hydrogen, a halogen, a nitro group, a cyano group, an alkyl group, a halogen substituted alkyl group and an alkylsulfonyl group.

5. Compound of formula:

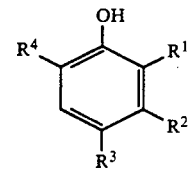

wherein
$R^2$ is an alkyl or alkoxy group;
$R^1$, $R^3$ and $R^4$ are the same or different and are selected from the group consisting of a nitro group, halogen, a cyano group, an alkylsulfonyl group, and a halogen substituted alkyl group.

6. Compound of formula:

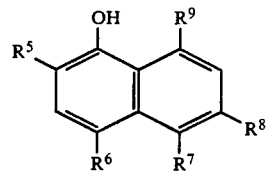

wherein
$R^7$ is an alkyl group, an alkoxy group or an aralkyl group, and
$R^5$, $R^6$, $R^8$ and $R^9$ are the same or different and are selected from the group consisting of a nitro group, halogen, a cyano group, an alkylsulfonyl group and a halogen substituted alkyl group, with the proviso that if $R^5$ and $R^6$ are nitro, $R^8$ and $R^9$ may be hydrogen.

7. Compound selected from the group consisting of:
[(2,3,5,6-tetrafluorophenyl)-hydrazono]propanedinitrile,
[(2-trifluoromethyl-4-nitrophenyl)-hydrazono]-propanedinitrile,
[(2-methanesulfonyl-4-nitrophenyl)-hydrazono]-propanedinitrile,
[(2,4-dinitro-6-cyanophenyl)-hydrazono]propanedinitrile and
[(3,5-di-{trifluoromethyl}phenyl)-hydrazono]-propanedinitrile.

* * * * *

UNITED STATES PATENT AND TRADEMARK OFFICE
CERTIFICATE OF CORRECTION

PATENT NO. : 5,215,924
DATED : June 1, 1993
INVENTOR(S) : Walter Rittersdorf, et al.

It is certified that error appears in the above-indentified patent and that said Letters Patent is hereby corrected as shown below:

Col. 2, lines 25-35:     change

"------------------------------------------------------------

Aqueous phase
          $Ion^+$                    $H^+$

Phase interface
_____

Ionophore + H-indicator    $(ion\text{-}ionophore)^+$  $indicator^-$

Organic phase
------------------------------------------------------------"

to

UNITED STATES PATENT AND TRADEMARK OFFICE
CERTIFICATE OF CORRECTION

PATENT NO. : 5,215,924          Page 2 of 3
DATED      : June 1, 1993
INVENTOR(S): Walter Rittersdorf, et al.

It is certified that error appears in the above-indentified patent and that said Letters Patent is hereby corrected as shown below:

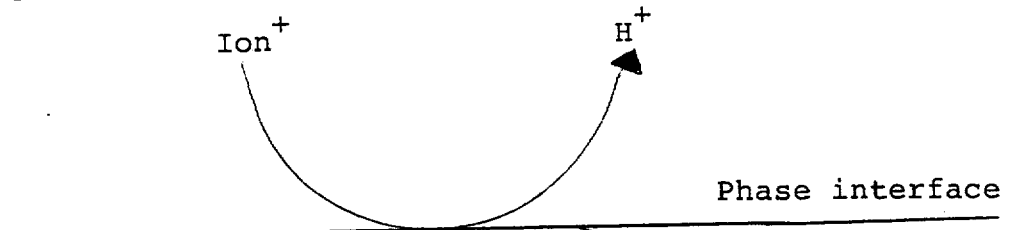

UNITED STATES PATENT AND TRADEMARK OFFICE
CERTIFICATE OF CORRECTION

PATENT NO. : 5,215,924
DATED : June 1, 1993
INVENTOR(S) : Walter Rittersdorf, et al.

It is certified that error appears in the above-indentified patent and that said Letters Patent is hereby corrected as shown below:

Col. 8, line 48:       change "R14" to -- $R^{14}$ --.

Col. 18, line 38:
(formula IX)      change " 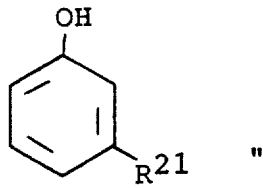 "

to -- 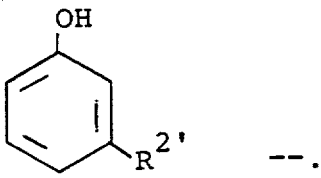 --.

Col. 25, line 26:      change "With" to -- with --.

Signed and Sealed this

Eighteenth Day of October, 1994

Attest:

BRUCE LEHMAN

Attesting Officer      Commissioner of Patents and Trademarks